(12) United States Patent
Sugiyama et al.

(10) Patent No.: US 8,454,592 B2
(45) Date of Patent: Jun. 4, 2013

(54) MEDICAL DEVICE SYSTEM FOR DETERMINING CONTACT BETWEEN FIRST MEDICAL DEVICE AND SECOND MEDICAL DEVICE

(75) Inventors: Yuta Sugiyama, Hachioji (JP); Kazuhiko Takahashi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 590 days.

(21) Appl. No.: 12/722,149

(22) Filed: Mar. 11, 2010

(65) Prior Publication Data

US 2010/0168744 A1 Jul. 1, 2010

Related U.S. Application Data

(63) Continuation of application No. PCT/JP2008/056948, filed on Apr. 8, 2008.

(30) Foreign Application Priority Data

Sep. 12, 2007 (JP) .................................. 2007-237046

(51) Int. Cl.
*A61B 18/18* (2006.01)

(52) U.S. Cl.
USPC ............................................. 606/35; 600/117

(58) Field of Classification Search
USPC ................. 600/103, 104, 117, 118, 134, 372, 600/373, 374; 606/34, 35, 46
See application file for complete search history.

(56) References Cited

U.S. PATENT DOCUMENTS

| 6,402,737 B1 | 6/2002 | Tajima et al. | |
| 7,171,286 B2 * | 1/2007 | Wang et al. | 700/248 |
| 2003/0216715 A1 * | 11/2003 | Moll et al. | 606/1 |
| 2004/0059322 A1 * | 3/2004 | Kawai et al. | 606/32 |
| 2005/0267335 A1 * | 12/2005 | Okada et al. | 600/173 |
| 2007/0013336 A1 * | 1/2007 | Nowlin et al. | 318/568.21 |
| 2009/0163907 A1 * | 6/2009 | Jarrard et al. | 606/35 |
| 2009/0192524 A1 * | 7/2009 | Itkowitz et al. | 606/130 |
| 2009/0209809 A1 * | 8/2009 | Schaller et al. | 600/103 |
| 2010/0168517 A1 * | 7/2010 | Shim et al. | 600/117 |

FOREIGN PATENT DOCUMENTS

| EP | 1 607 037 | 12/2005 |
| JP | 08-275958 | 10/1996 |
| JP | 2002-336269 | 11/2002 |

(Continued)

OTHER PUBLICATIONS

International Search Report dated May 13, 2008, in PCT/JP2008/056948.

*Primary Examiner* — Linda Dvorak
*Assistant Examiner* — Jocelyn D Ram
(74) *Attorney, Agent, or Firm* — Scully, Scott, Murphy & Presser, P.C.

(57) ABSTRACT

The medical device system includes: first and second medical devices that are used in the body cavity and surfaces of which have conductivity; a first electrode electrically connected to the surface of the first medical device; a second electrode electrically connected to the surface of the second medical device; a resistance measuring unit for measuring an inter-device resistance value between the first electrode and the second electrode; a threshold storing unit for storing a predetermined lower limit threshold of the inter-device resistance value; a determining unit for determining, when the inter-device resistance value is lower than the inter-device resistance threshold, that the first medical device and the second medical device come into contact with each other; and a warning generating unit for generating a warning.

9 Claims, 13 Drawing Sheets

FOREIGN PATENT DOCUMENTS

| | | |
|---|---|---|
| JP | 2004-081277 | 3/2004 |
| JP | 2004-89591 A | 3/2004 |
| JP | 2005-334237 A | 12/2005 |
| JP | 2007-029232 | 2/2007 |

* cited by examiner

MEDICAL DEVICE SYSTEM FOR DETERMINING CONTACT BETWEEN FIRST MEDICAL DEVICE AND SECOND MEDICAL DEVICE

CROSS REFERENCE TO RELATED APPLICATION

This application is a continuation application of PCT/JP2008/056948 filed on Apr. 8, 2008 and claims benefit of Japanese Application No. 2007-237046 filed in Japan on Sep. 12, 2007, the entire contents of which are incorporated herein by this reference.

BACKGROUND OF INVENTION

1. Field of the Invention

The present invention relates to a medical device system, and, more particularly to a medical device system having plural medical devices that are likely to come into contact with one another in a body cavity.

2. Description of the Related Art

In recent years, so-called endoscopic surgery that can minimize invasion in a patient compared with surgical operation involving laparotomy, thoracotomy, and the like has been performed. In particular, laparoscopic surgical operation is widely performed. This laparoscopic surgical operation is an operation performed by using a medical device inserted through a small dissected opening of the skin of a patient. In the laparoscopic surgical operation, after $CO_2$ is injected into an abdominal cavity to form a space necessary for the operation as pneumoperitoneum, a medical device having an elongated insertion portion is inserted through a trocar (a mantle tube) pierced into an epigastria region while the region being observed by an endoscope and the operation is performed.

Japanese Patent Application Laid-Open Publication No. 2004-81277 discloses an endoscope added with a function for detecting, when a surgical device used for the endoscopic surgical operation comes into contact with the endoscope, the contact using an arranged sensor and avoiding the contact.

Japanese Patent Application Laid-Open Publication No. 2004-89591 discloses a medical device having an electric manipulator in the endoscopic surgical operation.

Specifically, the sensor for detecting the contact between the surgical device and the endoscope disclosed in Japanese Patent Application Laid-Open Publication 2004-81277 is a gyro sensor and detects the contact as angular velocity.

In the medical device having the electric manipulator disclosed in Japanese Patent Application Laid-Open Publication No. 2004-89591, medical devices located at distal ends of two manipulators are medical devices to which positive voltage is alternately applied. However, a purpose of this voltage application is to burn and stanch a diseased part.

SUMMARY OF THE INVENTION

In order to attain the object, a medical device system according to the present invention includes: first and second medical devices, each of which is used in a body cavity and surfaces of which have conductivity; a first electrode electrically connected to the surface of the first medical device; a second electrode electrically connected to the surface of the second medical device; a resistance measuring unit for measuring an inter-device electric resistance value as electric resistance between the first electrode and the second electrode; a threshold storing unit for storing an inter-device resistance threshold as a predetermined lower limit value of the inter-device resistance value; a determining unit for determining, when the inter-device resistance value is lower than the inter-device resistance threshold, that the first medical device and the second medical device have come into contact with each other; and a warning generating unit for generating a warning when the determining unit determines that the first medical device and the second medical device have come into contact with each other.

DETAILED DESCRIPTION OF THE PREFERRED EMBODIMENT(S)

Embodiments of the present invention are explained below with reference to the drawings.

<Configuration of a Medical Device System>

Figure 1:
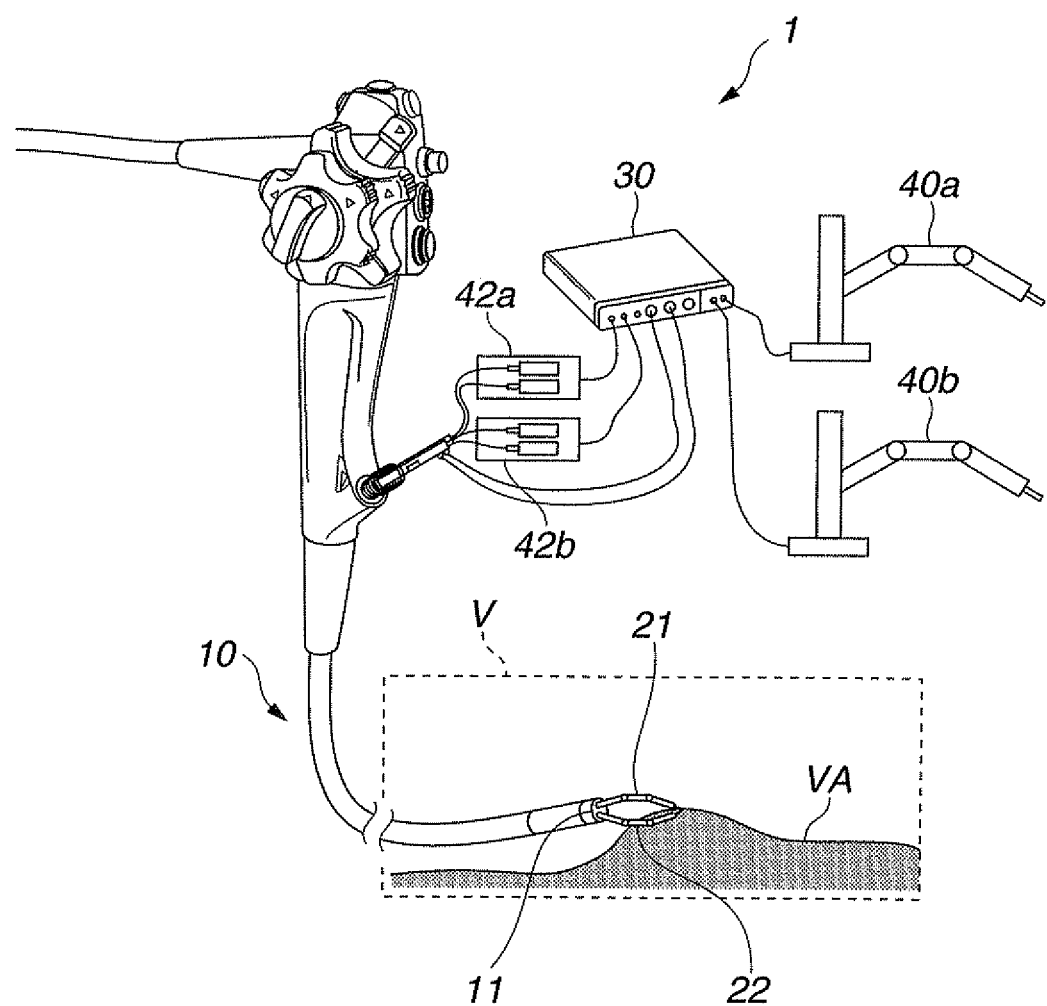
FIG. 1 is a configuration diagram of a medical device system according to a first embodiment.

A medical device system 1 according to a first embodiment of the present invention as shown in FIG. 1 includes an endoscope 10 including an observation lens 11 at a distal end thereof, a first medical device 21, a second medical device 22, driving units 42a and 42b, a control device 30, and input units 40a and 40b.

The first medical device 21 and the second medical device 22 project from a distal end portion of the endoscope 10 inserted in vivo and are used for performing an operation on a living tissue VA in body cavity V. The first medical device 21 and the second medical device 22 are active medical devices that are electrically driven with input information from the respective manual-operation input unit 40a and 40b transmitted to the respective driving units 42a and 42b via the control device 30. The manual-operation input units 40a and 40b are input units for converting three-dimensional motion of operation arms of an input device by a surgeon, i.e., physical displacement of the input device into an electric signal.

The respective manual-operation input units are devices adjusted to the respective medical devices. For example, when the medical devices have two joints, the manual-operation input unit also have two joints. Therefore, the surgeon can apply desired operation to the medical devices by operating the manual-operation input unit. When a motion amount of the medical devices is set small with respect to an actual physical displacement amount of the operation arms of the manual-operation input unit, the surgeon can easily realize extremely fine motion of the medical devices.

Figure 2:
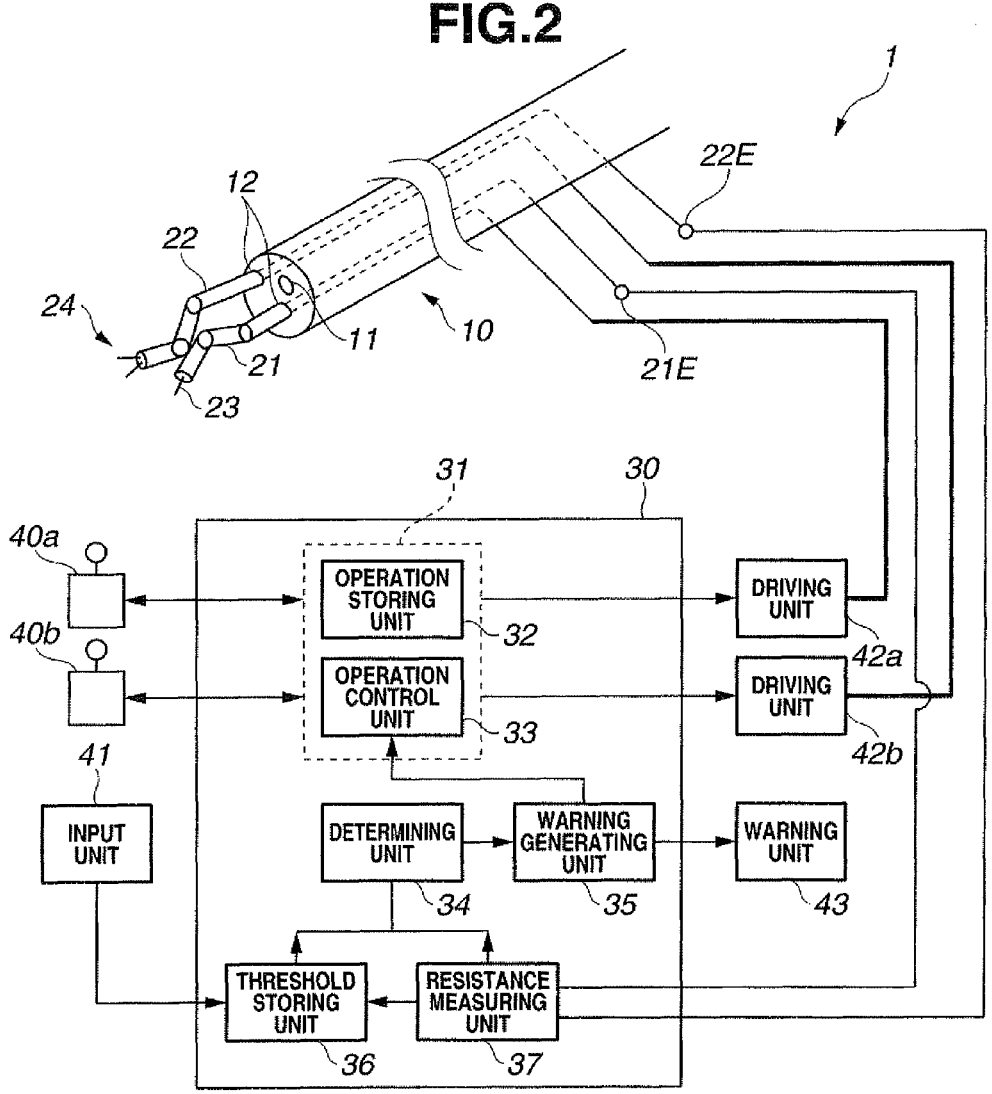
FIG. 2 is a block diagram of a medical device system 1 according to the first embodiment.

Next, as shown in FIG. 2, the first medical device 21 and the second medical device 22 project from forceps holes 12 at the distal end portion of the endoscope 10. Surfaces of the medical devices have conductivity. This does not mean that the medical devices themselves do not always need to be made of a conductive material, for example, SUS and the surfaces of the medical devices at least have to be coated with a material having conductivity. The medical device system 1 includes a first electrode 21E electrically connected to the surface of the first medical device 21 by an electric wire and a second electrode 22E electrically connected to the surface of the second medical device 22 by an electric wire. Electric resistance between the first electrode 21E and the second electrode 22E, i.e., an inter-device electric resistance value is measured by a resistance measuring unit 37.

The first medical device 21 and the second medical device 22 respectively have a knife arm 23 and hand arms 24. The first medical device 21 and the second medical device 22 are active medical devices driven by the driving units 42a and 42b according to instructions from the respective input units 40a and 40b via the control unit 31. The control device 30 includes a threshold storing unit 36 for storing a threshold of inter-device resistance inputted from the input unit 41, a determining unit 34 for determining whether the inter-device resistance is smaller than the threshold of the inter-device resistance stored in the threshold storing unit 36, and a warning generating unit 35 for generating a warning on the basis of the determination of the determining unit 34. The warning generated by the a warning generating unit 35 is transmitted to the surgeon by publicly-known warning such as sound, light, or vibration of a warning unit 43. The warning generated by the warning generating unit 35 is transmitted to the control unit 31 as an electric signal. When the control unit 31 receives the warning signal, the control unit 31 controls to perform contact avoiding operation explained later.

The manual-operation input units 40a and 40b are different depending on a type of an electric driving mechanism for medical devices. As a manual-operation input unit for a biaxially operating medical device, a normal joystick can be used. In a medical device that can perform more complicated operation, the manual operation input unit called operation arms for converting three-dimensional motion of hands of a surgeon to front and back, up and down, and left and right into an electric signal is used. In both the manual-operation input units, the motion of the hands of the surgeon is detected by sensors or the like disposed in the manual-operation input unit. Information concerning physical displacement of the manual-operation input unit is converted into an electric signal.

The manual-operation input units 40a and 40b themselves have not-shown driving mechanisms. By using the manual-operation input units 40a and 40b having the driving mechanisms, contrary to converting the motion of the hands of the surgeon into an electric signal, it is possible to generate force in an opposite direction against operation of the operation arms or the like by the motion of the hands of the surgeon to restrict the motion of the hands of the surgeon or change displacement of the operation arms or the like according to motion of the active medical devices unrelated to the surgeon as explained later.

The control device 30 may have an operation storing unit 32. The operation storing unit 32 stores, together with elapsed time, operation of the first medical device 21 and the second medical device 22 by the operation control unit 33 and displacement of the manual-operation input units 40a and 40b.

Figure 3A:
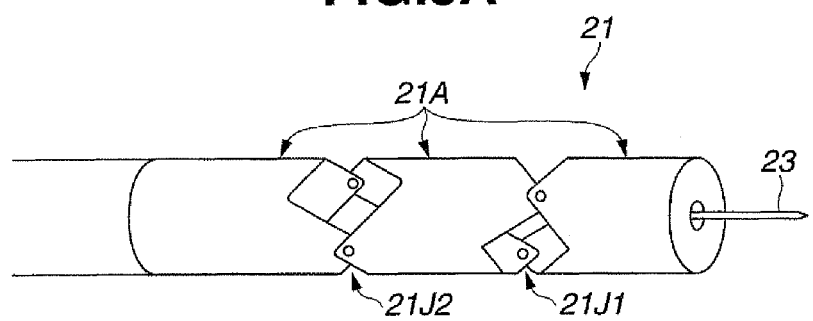
FIG. 3A is a perspective view of a first medical device.
Figure 3B:
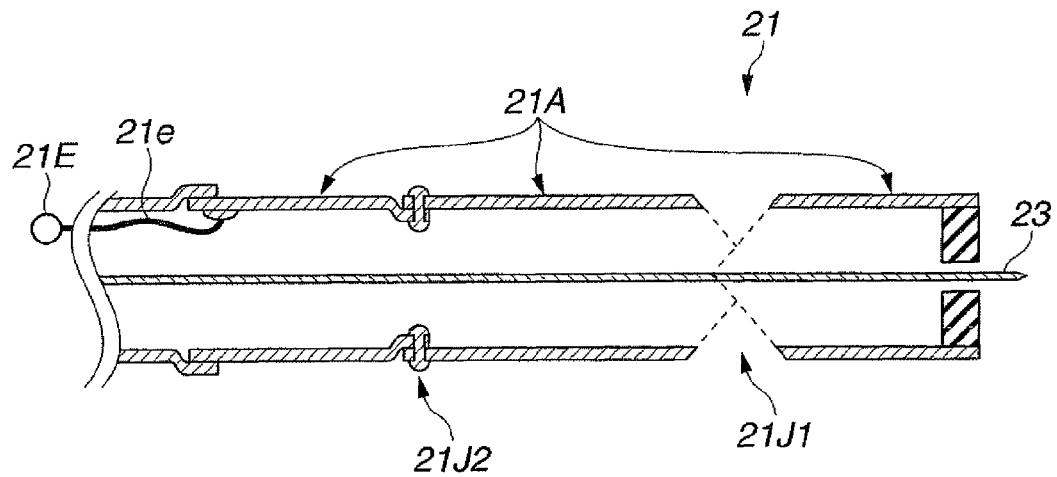
FIG. 3B is a sectional view in a longitudinal vertical direction of the first medical device.

Next, an example of the first medical device 21 according to the present embodiment is explained with reference to FIGS. 3A and 3B. As shown in FIG. 3A, the first medical device 21 has two bendable joints 21J1 and 21J2. Not-shown wires are connected to the two joints 21J1 and 21J2. The respective wires are connected to the driving units 42a and 42b. The two joints 21J1 and 21J2 are bendable according to advance and retract of the wires. The first medical device 21 is made of SUS. Even if the first medical device 21 is joined via the two joints 21J1 and 21J2, since links of bending portions are formed of a highly conductive raw material, for example, SUS, the first medical device 21 electrically has integrated structure. An electric wire 21e is connected from a connecting section provided in an inside thereof to the electrode 21E.

A knife arm 23 is inserted through the first medical device 21. A distal end of the first medical device 21 is made of an insulating material for electric insulation from the knife arm 23. However, a surface 21A of the first medical device 21 other than the distal end has conductivity.

The second medical device 22 is also a multi-joint manipulator having a configuration similar to that of the first medical device 21. Therefore, the medical device system 1 according to the present embodiment can detect contact between the first electrode of the first medical device and the second electrode of the second medical device by measuring electric resistance between the first electrode of the first medical device and the second electrode of the second medical device.

<Operation of the Medical Device System>

Next, operation of the medical device system 1 according to the present embodiment is explained with reference to FIGS. 4A to 8.

Figure 7:
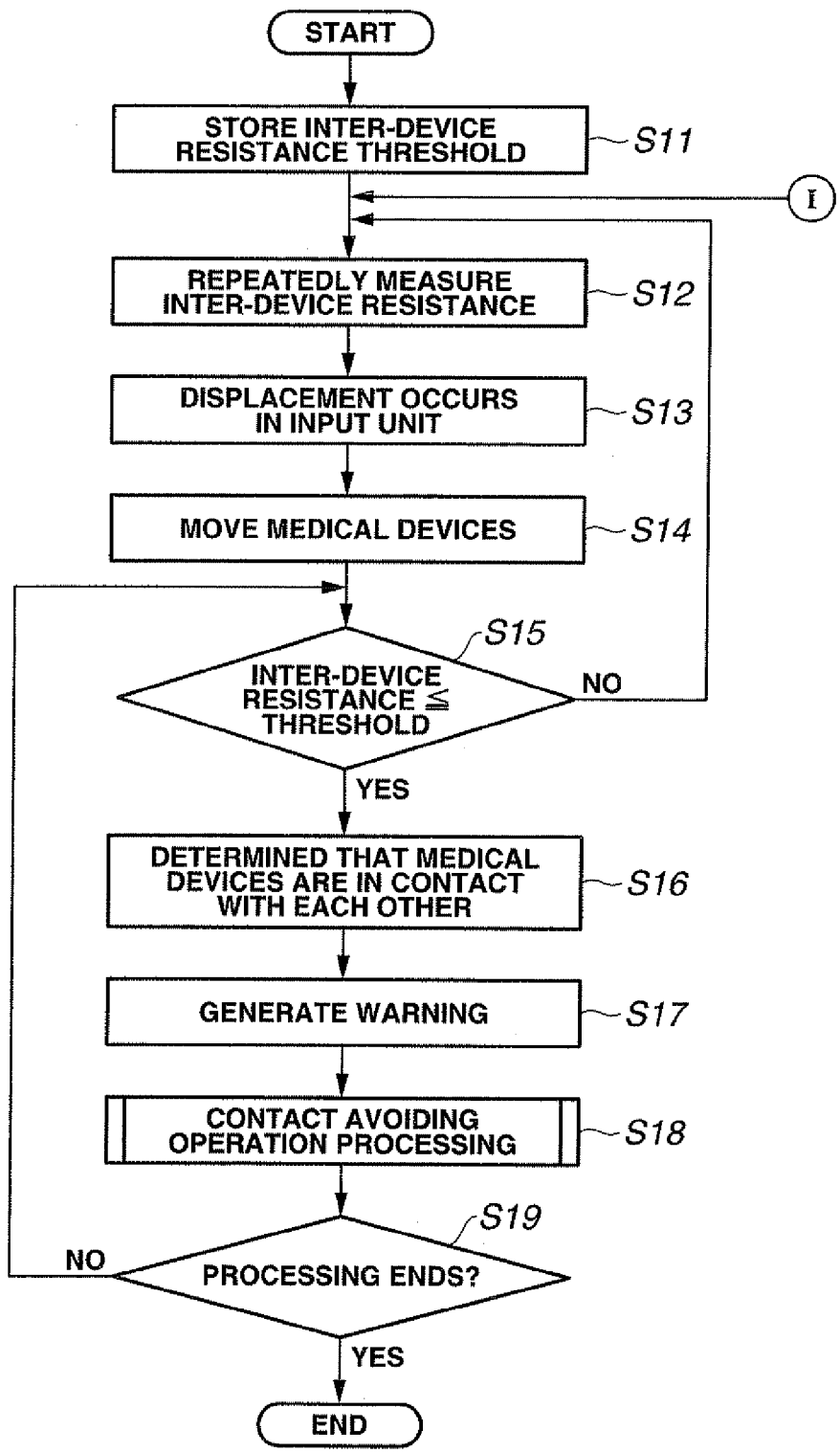
FIG. 7 is a flowchart for explaining a flow of operation of the medical device system.

The flow of the operation of the medical device system 1 according to the present embodiment is explained below according to the flowchart shown in FIG. 7.

When the endoscope 10 is inserted into a body cavity V and reaches a target region, the first medical device 21 and the second medical device 22 are projected from the forceps holes 12 to start treatment. In other words, the first medical device 21 and the second medical device 22 are projected from the distal end portion of the endoscope 10 and used. The first medical device 21 and the second medical device 22 may be projected when the endoscope 10 is inserted.

<Step S11>

The threshold storing unit 36 stores an inter-device resistance threshold Rc inputted by the surgeon using the input unit. The inter-device resistance threshold Rc is a predetermined lower limit value as a reference for the determining unit 34 to determine, when inter-device resistance R is smaller than the inter-device resistance threshold Rc, that the first medical device 21 and the second medical device 22 are in contact with each other.

As the inter-device resistance threshold Rc, a value stored by an another storing unit in advance, a value inputted from the surgeon using the input unit 41, or the like is used. For example, the inter-device resistance threshold Rc is desirably 0.1 to 1000 ohms and, particularly desirably 5 to 10 ohms. When the inter-device resistance threshold Rc is smaller than the range, in some cases, it is determined by the determining unit that the first medical device 21 and the second medical device 22 are in non-contact with each other although the medical devices are actually in contact with each other. When the inter-device resistance threshold Rc exceeds the range, in some cases, it is determined that the first medical device 21 and the second medical device 22 are in contact with each other although the medical devices are actually in non-contact with each other.

It is also possible to calculate the inter-device resistance threshold Rc from an inter-device resistance value R1 at the start of operation of the medical device system 1. Specifically, the inter-device resistance value R1 at the start of the operation of the medical device system 1 is a resistance value R1 at the time when the first medical device 21 and the second medical device 22 are in non-contact with each other not only directly but also indirectly via the living tissue VA. It is advisable to set a resistance value of, for example, one tenth of this resistance value R1 as the inter-device resistance threshold Rc.

Depending on a living tissue, since a resistance value thereof is relatively small, when the first medical device 21 and the second medical device 22 indirectly come into contact with each other via the living tissue VA, in some cases, inter-device resistance Rr indicates a low value and the determining unit 34 malfunctions. In this case, the inter-device resistance threshold Rc is set lower than usual. Alternatively, an inter-device resistance value R2 at the time when the first medical device 21 and the second medical device 22 are indirectly in contact with each other via the living tissue VA, which is actually being treated, may be measured by the resistance measuring unit 37 and the inter-device resistance threshold Rc may be calculated from R2.

<Step S12>

Measurement of inter-device resistance value by the resistance detecting unit 37 is started.

It is advisable to set electric current and voltage used for measurement of an inter-device resistance value by the resistance detecting unit 37 to feeble electric current and voltage that do not damage the living tissue VA, for example, 0.1 to 10 V and 0.1 to 500 mA. When the electric current and the voltage are smaller than the ranges, in some cases, accurate resistance measurement is difficult because of noise or the like. When the electric current and the voltage are equal to or larger than the ranges, in some cases, the living tissue VA is damaged.

For the measurement of an inter-device resistance value by the resistance detecting unit 37, it is unnecessary to continuously apply the electric current and the voltage. The electric current and the voltage may be intermittently applied to measure resistance. The measurement of an inter-device resistance value may be performed by any one of driving systems, i.e., constant current driving and constant voltage driving. The measurement of an inter-device resistance value may be performed by an alternating current rather than a direct current.

Figure 5A:
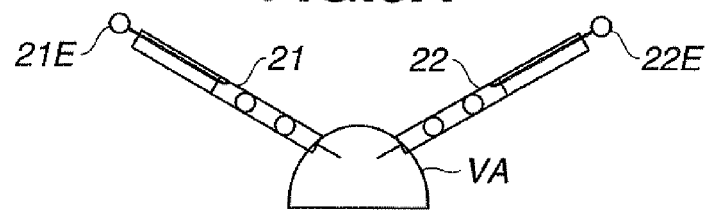
FIGS. 5A and 5B are diagrams for explaining an inter-device electric resistance value between a surface of the first medical device and a surface of the second medical device.
Figure 5B:
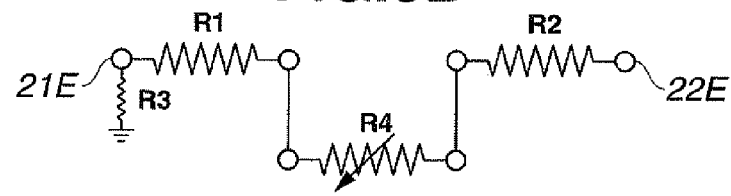

An inter-device electric resistance value at a stage when the measurement of an inter-device resistance value is started is explained with reference to FIGS. 5A and 5B. FIG. 5A shows a state in which the first medical device 21 and the second medical device 22 are electrically in contact with each other via the living tissue VA. FIG. 5B shows resistance in the state. An inter-device resistance value between the first electrode 21E and the second electrode 22E is a sum (R1+R2+R4) of resistance R1 of the first medical device 21 itself, resistance R2 of the second medical device 22 itself, and resistance R4 of the living tissue VA. The resistance R4 of the living tissue VA is a value that changes according to, for example, a positional relation between the first medical device 21 and the second medical device 22. R3 is resistance from the first electrode 22E to the ground and can be arbitrarily set.

R1, R2, and R3 are resistances of a conductive material and are extremely low compared with the resistance R4 of the living tissue VA. In other words, since R4>>R1, R2, and R3, the inter-device resistance value (R1+R2+R4) is substantially (R4).

It is evident that an inter-device resistance value in a state in which the first medical device 21 and the second medical device 22 are not in contact with the living tissue VA is extremely large resistance due to a leak current or the like.

<Step S13>

Physical displacement occurs in the operation arm of the manual-operation input unit 40a because of the operation by the surgeon.

<Step S14>

Figure 4A:
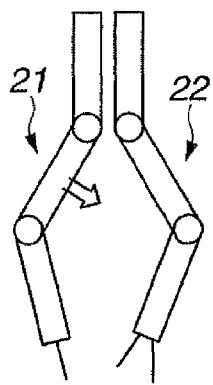
FIGS. 4A to 4F are diagrams for explaining driving states of the first medical device and a second medical device.
Figure 4B:
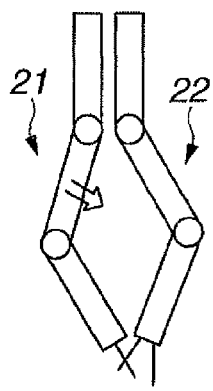

According to the physical displacement of the manual-operation input unit 40a converted into an electric signal, the operation control unit 33 drives the driving unit 42a and, as shown in FIGS. 4A to 4B, the first medical device 21 starts movement.

<Step S15>

Figure 4C:
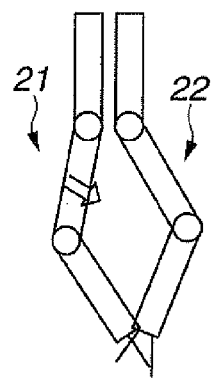

Next, an inter-device resistance value in the case in which the first medical device 21 and the second medical device 22 come into contact with each other as shown in FIG. 4C is explained with reference to FIGS. 6A and 6B.

Figure 6A:
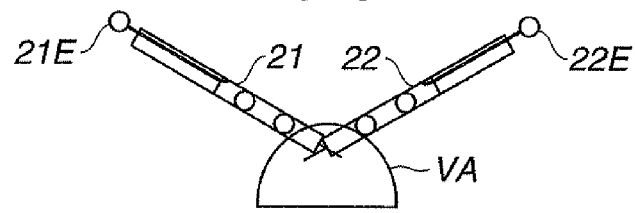
FIGS. 6A and 6B are diagrams for explaining an inter-device electric resistance value between the surface of the first medical device and the surface of the second medical device.
Figure 6B:
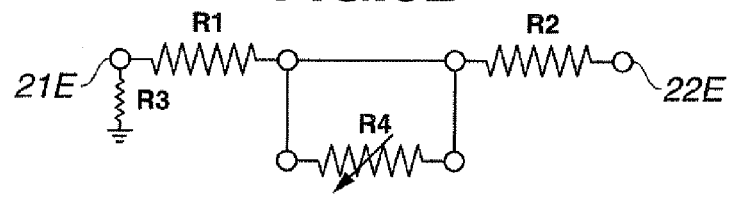

When the first medical device 21 comes into contact with the second medical device 22 as shown in FIG. 6A (YES), since the surfaces of both the medical devices have conductivity, resistance between the surfaces of both the medical devices is extremely low. Therefore, the inter-device resistance value between the first electrode 21E and the second electrode 22E can be regarded as a sum (R1+R2) of the resistance R1 of the first medical device 21 itself and the resistance R2 of the second medical device 22 itself. As explained in step S12, R4>>R1 and R2. The inter-device resistance value (R1+R2) is a value smaller than the inter-device resistance threshold Rc.

When the inter-device resistance value is higher than the inter-device resistance threshold Rc (NO), the control device 30 returns to step S12 and continues normal control.

<Step S16>

When the inter-device resistance value decreases to be lower than the inter-device resistance threshold Rc, the determining unit 34 determines that the first medical device 21 and the second medical device 22 come into contact with each other and sends a signal to the warning generating unit 35.

<Step S17>

The warning generating unit 35 generates warning according to the determination by the determining unit 34 that the first medical device 21 and the second medical device 22 come into contact with each other. The warning is transmitted to the surgeon by a publicly-known warning method.

<Step S18>

The warning generated by the warning generating unit 35 is transmitted to the control unit 31 as an electric signal. When the control unit 31 receives the warning signal, the control unit 31 controls to perform contact avoiding operation processing explained later.

<Step S19>

When the inter-device resistance value increases to be higher than the inter-device resistance threshold Rc according to contact avoiding operation, i.e., when the contact is released, the control device 30 returns to (I) and continues the normal control until a treatment end instruction is received (YES).

Figure 8:
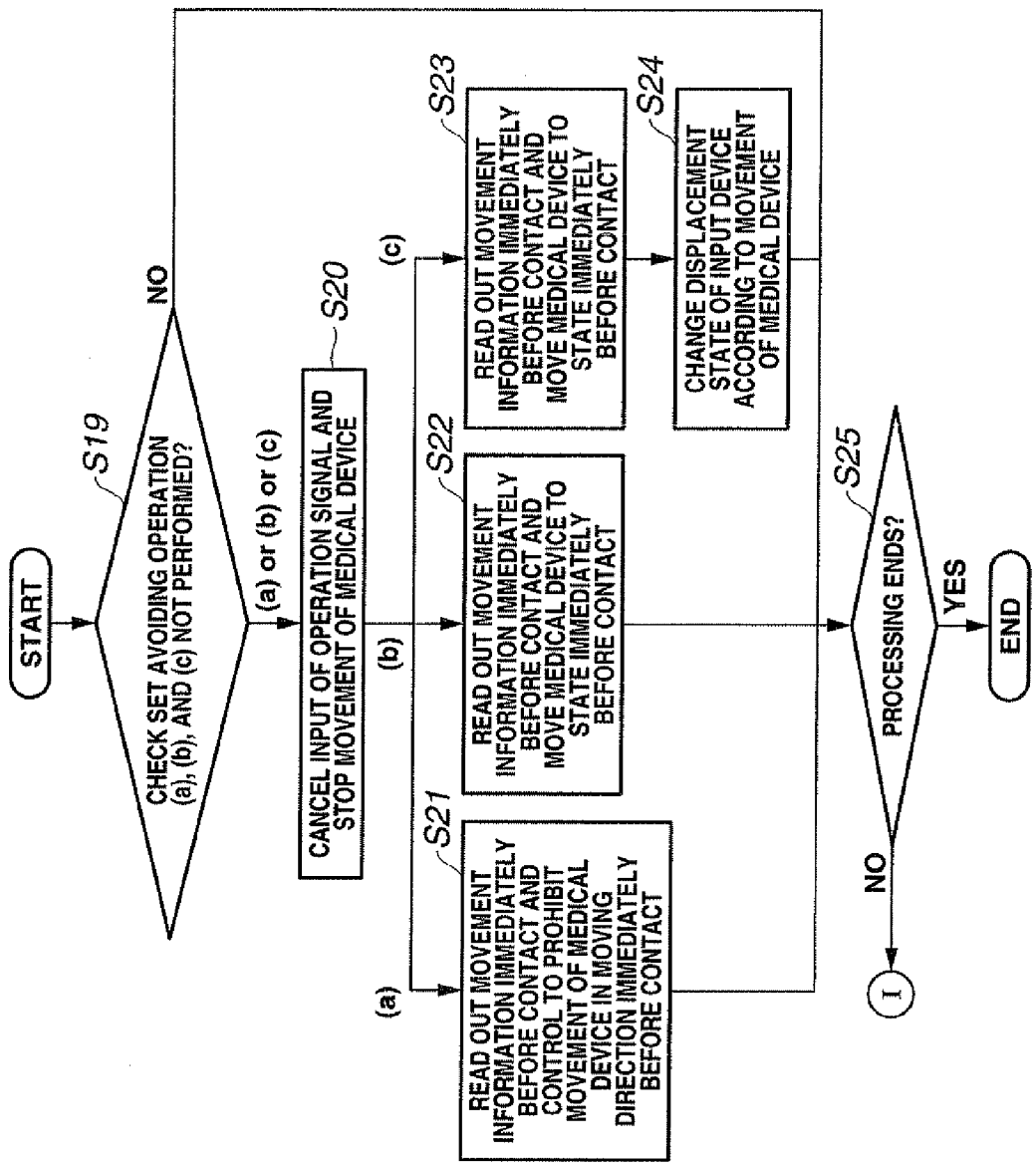
FIG. 8 is a flowchart for explaining a flow of operation of the medical device system.

Next, contact avoiding operation is explained with reference to FIG. 8. The control unit 31 of the medical device system 1 according to the present embodiment can also perform auxiliary operation when the surgeon learns occurrence of contact according to warning and performs operation for contact release.

<Step S19>

The control unit 31 checks whether treatment of any one of contact avoiding operations (a), (b), and (c) selected by the surgeon in advance is performed or the avoiding operation control is not performed when warning is generated by the warning generating unit 35, i.e., when a warning signal is received from the warning generating unit 35.

<Step S20>

The control unit 31 of the medical device system 1 according to the present embodiment can avoid further contact by performing control for stopping the operation of the driving units 42a and 42b when warning is generated by the warning generating unit 35.

Figure 4D:
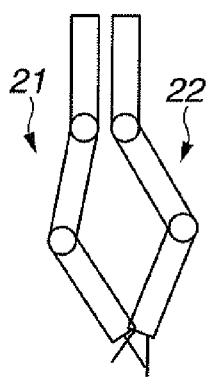

Specifically, the control unit 31 cancels all inputs of operations signals by the operation arm of the manual-operation input unit 40a and stops moving operation of the first medical device 21 as shown in FIG. 4D.

<Step S21>

Since the operation of the first medical device is stopped, damage to the medical device and the like due to further contact are prevented. To continue the treatment again, it is necessary to perform moving operation for safely separating the first medical device 21 from the second medical device 22.

In the medical device system 1 according to the present embodiment, the operation storing unit 32 has stored therein operation information of the driving unit, i.e., operation information of the medical devices. Therefore, the control unit 31 can control, on the basis of the operation information stored by the operation storing unit 32, the driving unit 31 to prohibit further movement in a moving direction in which the first medical device 21 moves before the control unit 31 receives warning, i.e., before contact occurs. Prohibiting the movement means that, even if a moving instruction from the input unit or the like by the surgeon is received, the instruction is cancelled and is not executed.

Figure 4E:
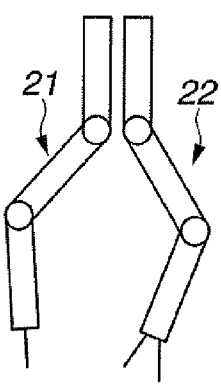

Therefore, the surgeon can safely separate the first medical device 21 from the second medical device 22 by moving the first medical device 21 in a movable direction different from the moving direction of the first medical device before the contact as shown in FIG. 4E.

Specifically, for example, when a moving direction of the medical device 21 immediately before the contact is a certain direction vector (+X, -Y, +Z) in a three-dimensional space, the control unit 31 can avoid further contact between the medical devices by prohibiting movement in the (+X, -Y, +Z) direction and allowing the first medical device 21 to move only in an opposite vector direction.

<Step S22>

Figure 4F:
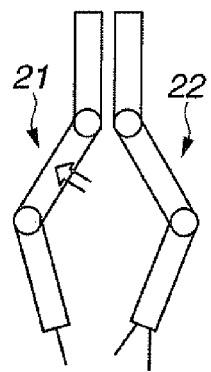

In the medical device system 1 according to the present embodiment, the operation storing unit 32 has stored therein the operation information of the driving unit, i.e., the operation information of the medical devices. Therefore, as shown in FIG. 4F, the control unit 31 can return a state of the driving unit 42a, i.e., a state of the first medical device 21 to a state before the control unit 31 receives warning, i.e., a state before the contact.

The surgeon selects a degree of returning the state of the first medical device 21 to the state before the contact occurrence. As a unit for returning the state of the first medical device 21 to the state before the contact occurrence, for example, an operation step unit of the driving unit, a time unit, or the like can be selected. However, for example, it is advisable to return the state of the first medical device 21 to a state two seconds before the contact occurrence.

<Steps S23 and S24>

In the medical device system 1 according to the present embodiment, the operation storing unit 32 has stored therein the operation of the first medical device. Therefore, the control unit 31 can control the driving unit to return the state of the driving unit 42a, i.e., the state of the first medical device 21 to the state before the warning occurrence by the warning generating unit 35, i.e., the state before the contact.

Further, the operation arm of the manual-operation input unit 40a can be returned to a position before the contact in the same manner as the return operation of the first medical device 21. Specifically, the control unit 31 performs control for returning a state of physical displacement of the manual-operation input unit having the driving mechanism to a state before the contact.

The surgeon can resume the operation after checking a returned state of the first medical device 21 according to a state change of the operation arm of the manual-operation input unit 40a. Step S23 and step S24 are simultaneously performed in parallel.

The contact avoiding operation and the returning operation are performed according to selection by the surgeon. The surgeon may select the operations in advance, may select the operation according to a state after contact occurrence, or may select another operation during or after the contact avoiding operation.

In the above explanation, the first medical device 21 moves. However, the same holds true in the case of contact occurrence due to movement of the second medical device 22 and when contact occurs while both the first medical device 21 and the second medical device 22 simultaneously move.

<Combination Examples of the Medical Devices>

Combinations of the medical devices as modifications of the first embodiment are explained with reference to FIGS. 9A to 9G. In the modifications of the first embodiment, one or both of the first medical device 21 and the second medical device 22 are active medical devises having a driving unit, for example, active treatment instruments or active endoscopes.

Figure 9A:
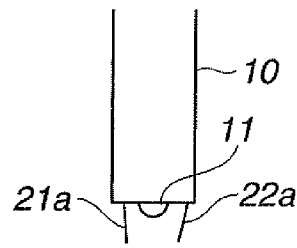
FIGS. 9A to 9G are diagrams for explaining a combination of a first medical device and a second medical device as a modification of the first embodiment.
Figure 9B:
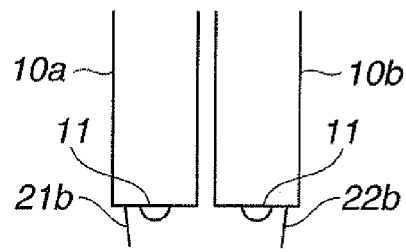
Figure 9C:
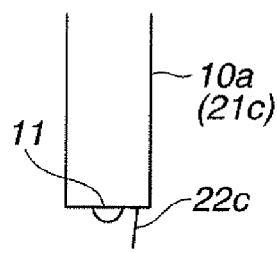
Figure 9D:
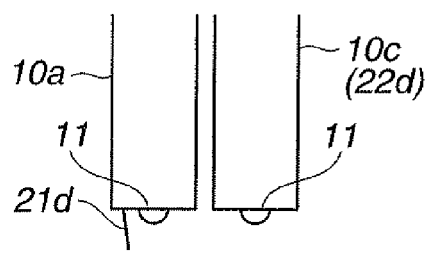

FIG. 9A is a case in which the first medical device 21 is an active treatment instrument 21a of the endoscope 10 and the second medical device 22 is an active treatment instrument 22a of the endoscope 10. FIG. 9B is a case in which the first medical device 21 is an active treatment instrument 21b of an endoscope 10a and the second medical device 22 is an active treatment instrument 22b of another endoscope 10b. FIG. 9C is a case in which the first medical device 21 is the endoscope 10a (21c) itself and the second medical device 22 is an active treatment instrument 22c of the endoscope 10a. FIG. 9D is a case in which the first medical device 21 is an active treatment instrument 21d of the endoscope 10a and the second medical device 22 is an endoscope 10c (22d) itself.

Figure 9E:
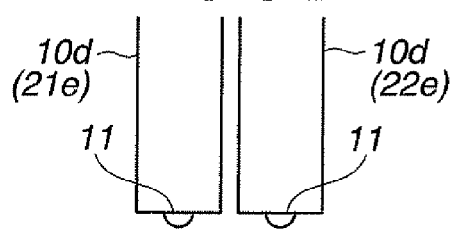
Figure 9F:
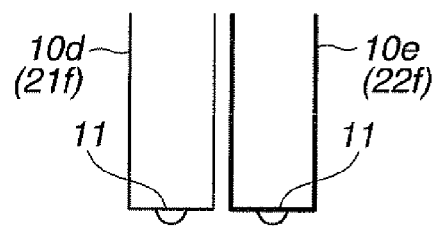
Figure 9G:
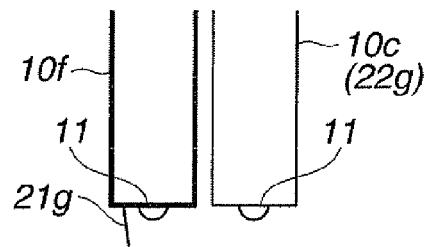

FIG. 9E is a case in which the first medical device 21 is an active endoscope 10d (21e) itself and the second medical device 22 is the active endoscope 10d (22e) itself. FIG. 9F is a case in which the first medical device 21 is the active endoscope 10d (21f) itself and the second medical device 22 is another rigid endoscope 10e (22f) itself. FIG. 9G is a case in which the first medical device 21 is an active treatment instrument 21g of a rigid endoscope 101 and the second medical device 22 is the active endoscope 10e (22g) itself.

Figure 10:
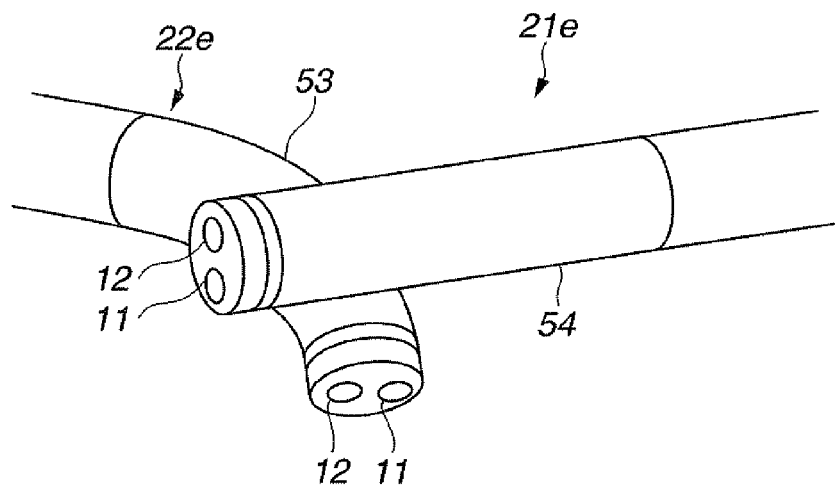
FIG. 10 is a diagram for explaining a combination of the first medical device and the second medical device as a modification of the first embodiment.

FIG. 10 shows a case in which the first medical device 21 is the active endoscope 21e and the second medical device 22 is another active endoscope 22e. The active endoscope 21e and the active endoscope 22e are respectively configured such that surfaces 53 and 54 thereof are conductive. Therefore, when the active endoscope 21e and the active endoscope 22e come into contact with each other, the control device 30 can detect the contact and perform the contact avoiding operation.

Figure 11:
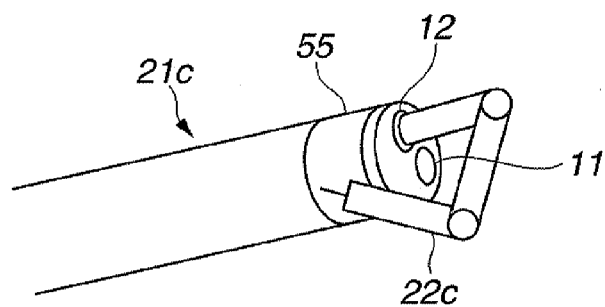
FIG. 11 is a diagram for explaining a combination of the first medical device and the second medical device as a modification of the first embodiment.

FIG. 11 shows a case in which the first medical device 21 is the endoscope 21c and the second medical device 22 is the active treatment instrument 22e of the endoscope 21c. Specifically, the first medical device 21 is the endoscope 21c and the second medical device 22 is projected from a distal end portion of the endoscope 21c and used. A surface 55 of the endoscope 2k and a surface of the active treatment instrument 22c are configured to be conductive. Therefore, when the endoscope 21c and the active treatment instrument 22c come into contact with each other, the control device 30 can detect the contact and perform the contact avoiding operation.

As explained above, various modifications of the medical devices according to the present embodiment are possible. It is also possible to combine the first medical device 21 and the second medical device 22 with other single or plural medical devices, contact among which does not need to be detected, or detect contact among three or more medical devices. When the contact among the three or more medical devices is detected, surfaces of all the medical devices as contact detection targets are made conductive and inter-device resistance among the medical devices is measured.

<Contact Detection According to a Resistance Ratio Through Use of a Human Body Electrode>

A contact detecting method by the medical device system 1 according to a second embodiment of the present invention is explained with reference to FIGS. 12 to 14B.

Figure 12:
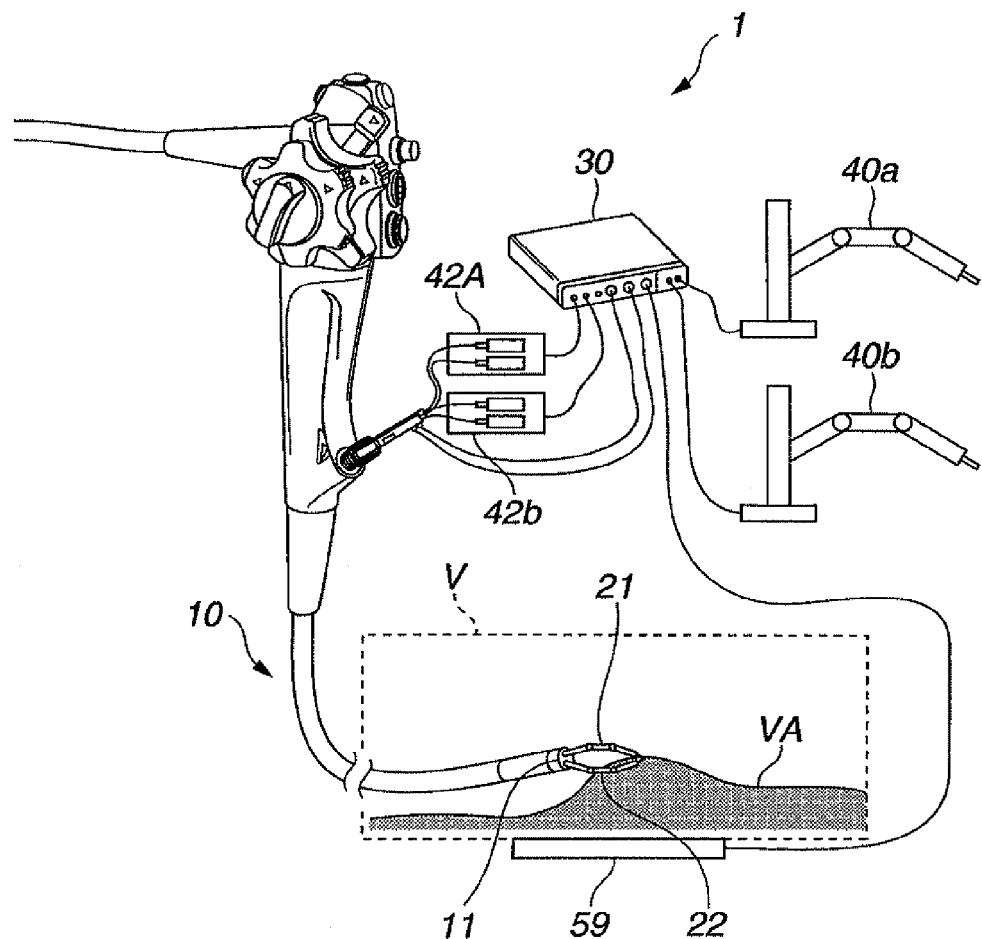
FIG. 12 is a configuration diagram of a medical device system according to a second embodiment.

As shown in FIG. 12, a basic configuration of the medical device system 1 according to the present embodiment is similar to that of the medical device system according to the first embodiment shown in FIGS. 1 and 2. However, the medical device system 1 according to the present embodiment includes a human body electrode plate 59 and a human body electrode 59E connected to the human body electrode plate 59. In order to come into contact with a living tissue as a part of a not-shown human body and measure electric resistance of an organism as a conductor, the human body electrode plate 59 is an electrode plate that is brought into contact with the human body. The resistance measuring unit 37 measures, together with an inter-device resistance value, an electrode-to-human body resistance value as electric resistance between the first electrode or the second electrode and the human body electrode.

Figure 13A:
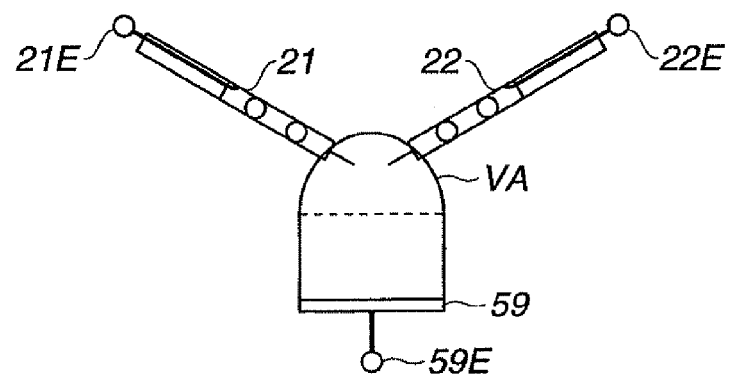
FIGS. 13A and 13B are diagrams for explaining an inter-device electric resistance value and an electrode-to-human body resistance value of the medical device system according to the second embodiment.
Figure 13B:
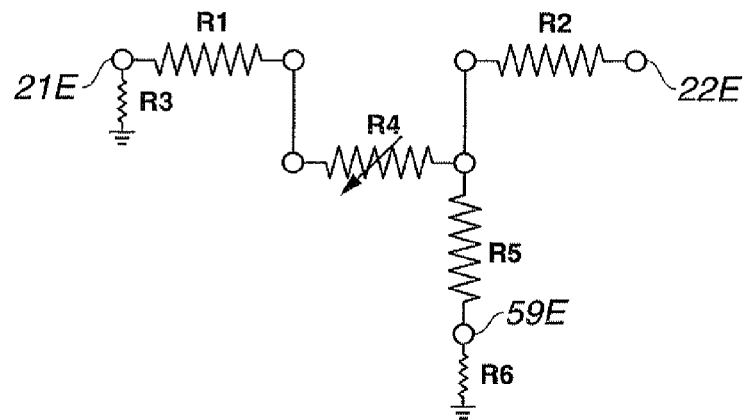

A resistance value at a stage when measurement of the inter-device resistance value and the electrode-to-human body resistance value is started is explained with reference to FIGS. 13A and 13B. FIG. 13A shows a state in which the first medical device 21 and the second medical device 22 are electrically in contact with each other via the living tissue VA. FIG. 13B shows resistance in the state.

The inter-device resistance value between the first electrode 21E and the second electrode 22E is a sum (R1+R2+R4) of the resistance R1 of the first medical device 21 itself, the resistance R2 of the second medical device 22 itself, and the resistance R4 of the living tissue VA. The resistance R4 of the living tissue VA is a value that changes according to, for example, a positional relation between the first medical device 21 and the second medical device 22. R3 and R6 are up resistance from the ground.

An electrode-to-human body resistance value as electric resistance between the second electrode and the human body electrode is a sum (R2+R5) of R5 as electric resistance of the human body and the resistance R2 of the second medical device 22 itself. Therefore, an electric resistance value ratio as a ratio of the inter-device electric resistance value and the electrode-to-human body resistance value is (R1+R2+R4)/(R2+R5). Since R5 as the electric resistance of the human body is higher than the resistance R4 of the living tissue VA, R5>>R4>>R1, R2, R3, and R6.

In a state in which the first medical device 21 and the second medical device 22 are not in contact with the living tissue VA, it is evident that the inter-device electric resistance value is an extremely large value and, as a result, the electric resistance value ratio is also an extremely large value.

Next, an inter-device resistance value in the case in which the first medical device 21 comes into contact with the second medical device 22 is explained with reference to FIG. 14B.

Figure 14A:
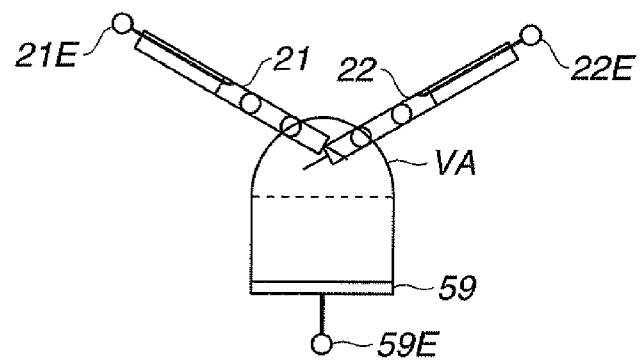
FIGS. 14A and 14B are diagrams for explaining an inter-device electric resistance value and an electrode-to-human body resistance value of the medical device system according to the second embodiment.
Figure 14B:
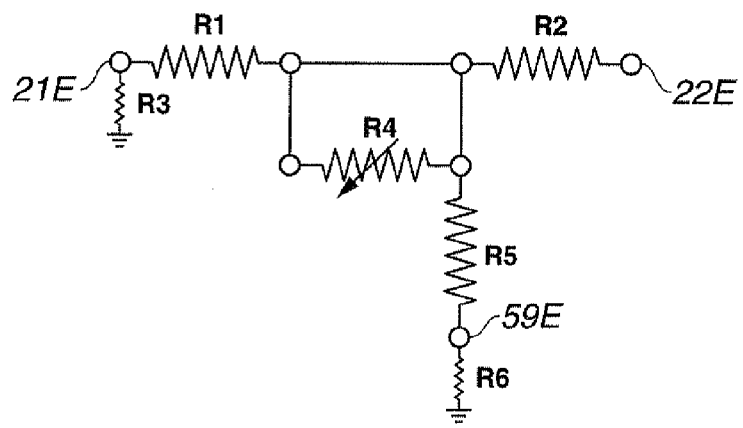

As shown in FIG. 14B, when the first medical device 21 comes into contact with the second medical device 22, since the surfaces of both the medical devices have conductivity, resistance between the surfaces of both the medical devices is extremely low. Therefore, the inter-device resistance value between the first electrode 21E and the second electrode 22E is substantially a sum (R1+R2) of the resistance R1 of the medical device 21 itself and the resistance R2 of the second medical device 22 itself. On the other hand, the electrode-to-human body resistance value does not change from (R2+R5). Therefore, the electric resistance value ratio as the ratio of the inter-device electric resistance value and the electrode-to-human body resistance value is (R1+R2)/(R2+R5). Therefore, it is evident that the electric resistance value ratio substantially decreases because of the contact. In other words, since the electric resistance value ratio substantially decreases from ½ to ¹/₁₀₀, it is possible to determine that the first medical device 21 comes into contact with the second medical device 22.

In the medical device system 1 according to the present embodiment, it is possible to determine presence or absence of contact on the basis of a ratio of electric resistances rather than level of electric resistances. Therefore, highly accurate contact detection is possible.

In the present embodiment, the electric resistance between the second electrode and the human body electrode is set as the electrode-to-human body resistance value. However, the same holds true when the electric resistance between the first electrode and the human body electrode is set as the electrode-to-human body resistance value.

<Contact Detection According to Electric Current or Voltage>

According to the first embodiment and the second embodiment, contact between the first medical device 21 and the second medical device 22 is determined according to electric resistance. On the other hand, it is also possible to determine contact between the first medical device 21 and the second medical device 22 according to electric current or voltage.

For example, in FIGS. 13B and 14B, when voltage V is applied to the second electrode 22E, voltage of the first electrode 21E and voltage of the human body electrode 59E are nearly zero in a complete non-contact state of the first medical device 21 and the second medical device 22. When the first medical device 21 and the second medical device 22 are in contact with each other via the living tissue VA, both the voltage of the first electrode 21E and the voltage of the human body electrode 59E are not zero. When the first medical device 21 and the second medical device 22 are in contact with each other, the voltage of the first electrode 21E is not zero but the voltage of the human body electrode 59E is nearly zero. It is possible to determine a contact state from such a voltage change.

Electric current, voltage, and resistance may be used for contact detection in combination.

<Division of a Conductive Area on the Surface of the Medical Device>

Next, as a modification of the medical device 21 or 22 according to the present embodiment, the medical device 21 or 22 with an area having conductivity of the surface thereof divided is explained with reference to FIGS. 15, 16A, and 16B.

Figure 15:
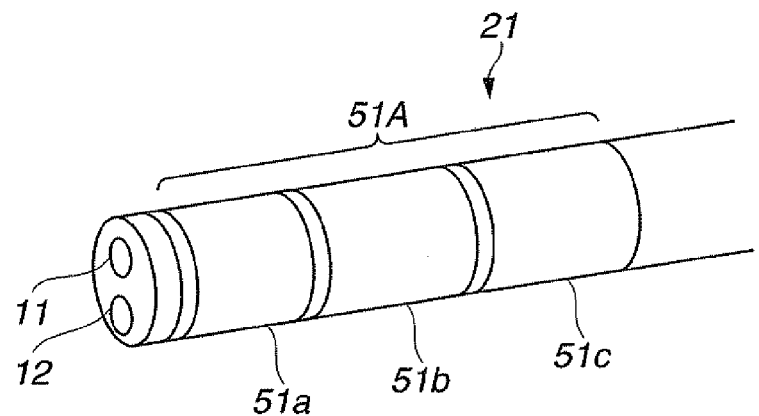
FIG. 15 is a diagram for explaining a modification of the medical device.

A conductive area 51A on the surface of the first medical device 21 shown in FIG. 15 is divided into three portions 51a, 51b, and 51c. Areas among the portions are nonconductive. Electrodes electrically connected to respective conductive area surfaces are provided. Therefore, when the first medical device 21 and the not-shown second medical device 22 come into contact with each other, it is seen which of the three portions 51a, 51b, and 51c of the first medical device 21 is in contact with the second medical device 22. Therefore, the surgeon can more safely take contact avoiding measures.

It goes without saying that, by dividing a conductive area on the surface of the not-shown second medical device 22 in the same manner, a contact place of the second medical device 22 is also known. The surgeon can more safely take contact avoiding measures.

Figure 16A:
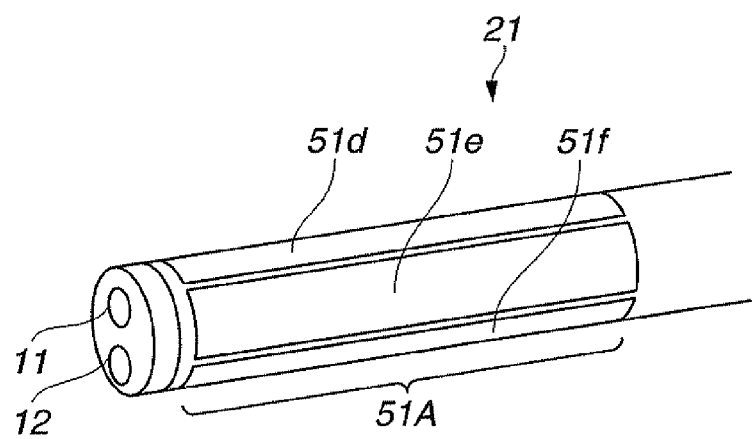
FIGS. 16A and 16B are diagrams for explaining a modification of the medical device.
Figure 16B:
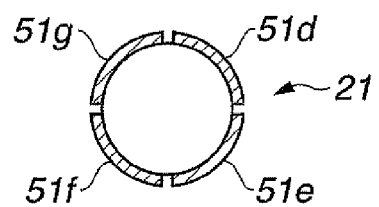

The conductive area 51A on the surface of the first medical device 21 shown in FIGS. 16A and 16B is divided into four portions 51d, 51e, 51f, and 51g in a circumferential direction as shown in a medical device longitudinal vertical direction sectional view of FIG. 16B. Areas among the portions are nonconductive. Therefore, when the first medical device 21 and the not-shown second medical device 22 come into contact with each other, it is seen in which direction the second medical device 22 is in contact with the first medical device. Therefore, the surgeon can more safely take contact avoiding measures.

When the medical device 21 or 22 has multi-link structure, an electrode may be formed for each of links. The medical device 21 or 22 having a large number of divided conductive surface areas can obtain more detailed information concerning a contact place.

<Associated Operation with an Electric Knife>

Figure 17:
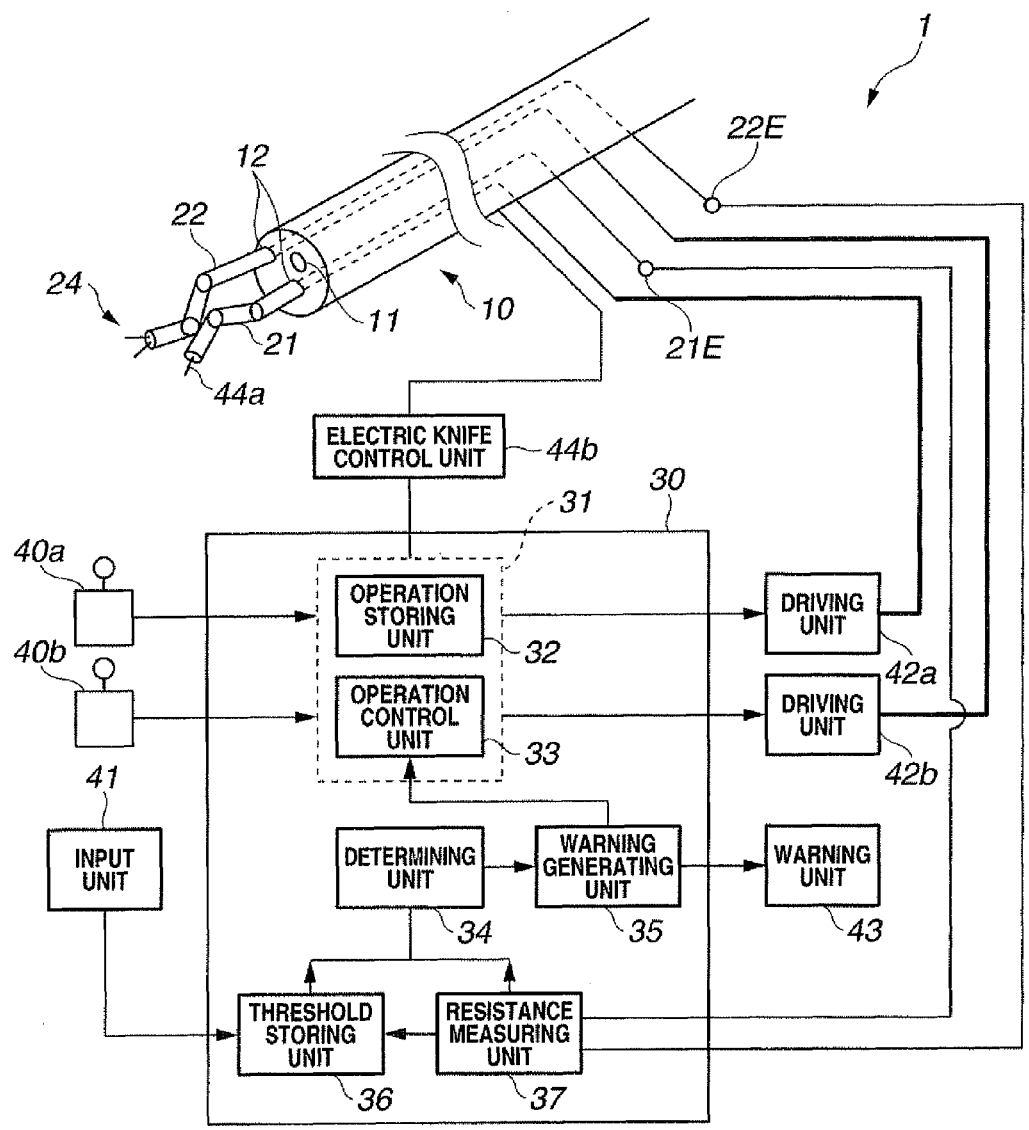
FIG. 17 is a block diagram of a medical device system having medical devices including electric knives.

Next, FIG. 17 is a block diagram of the medical device system 1 having the medical device 21 including an electric knife 44a. As shown in FIG. 17, the medical device system 1 according to the present embodiment includes the electric knife 44a in the first medical device 21 and further includes an electric knife control unit 44b, a not-shown high-frequency power supply, and the like for the electric knife 44a.

An electric knife device is used for performing treatment such as dissection, coagulation, and hemostasis for a living tissue. The electric knife device includes the electric knife control unit 44b, the not-shown high-frequency power supply connected to the electric knife control unit 44b, and the electric knife 44a. The electric knife device supplies high-frequency power from the high-frequency power supply to the electric knife 44a, which is brought into contact with the living tissue, and cauterizes the living tissue with energy of the high-frequency power.

When contact occurs between the medical devices 21 and 22 during treatment by the electric knife 44a, a high-frequency current flows through an unexpected path. Therefore, in the medical device system 1 according to the present embodiment, when contact occurs between the medical devices during use of the electric knife 44a provided in the medical device 21 or 22, the control unit 31 performs control for controlling the electric knife control unit 44b to stop or reduce output of the electric knife 44a.

As shown in FIG. 17, in the medical device system 1 according to the present embodiment, the control unit 31 performs control of the electric knife control unit 44b. When contact between the medical devices occurs and a warning signal is received from the warning generating unit 35, the control unit 31 sends a signal to the electric knife control unit 44b and stops or reduces output of the high-frequency power supply. The surgeon sets in the control unit 31 in advance what kind of control of the electric knife control unit should be performed.

Since a stray current due to a high-frequency current flows in the body cavity V of the patient during use of the electric knife 44a, it is difficult to measure inter-device electric resistance and the like. Therefore, high-frequency current application to the electric knife 44a and inter-device electric resistance measurement are performed to be timed to coincide with each other. Specifically, ON/OFF of the high-frequency current of the electric knife 44a is periodically repeated and inter-device current resistance is measured only while the high-frequency current of the electric knife 44a is OFF. Although an ON/OFF period of the high-frequency current is not specifically limited, about 1 to 1000 ms is desirable. Control is difficult when the ON/OFF period is smaller than the range. When the ON/OFF period exceeds the range, detection of contact between the medical devices is delayed.

In the medical device system 1 according to the present embodiment, when contact between the medical devices occurs, the output of the electric knife 44a stops or falls. Therefore, it is possible to more safely perform treatment.

The present invention is not limited to the embodiments above. Various modifications, alterations, and the like are possible in a range in which the gist of the present invention is not changed.

What is claimed is:

1. A medical device system comprising:
   first and second medical devices, each of which is used in a body cavity and surfaces of which have conductivity;
   a first electrode electrically connected to the surface of the first medical device;
   a second electrode electrically connected to the surface of the second medical device;
   a human body electrode plate that can come into contact with a surface of a human body outside of a body cavity;
   a human body electrode electrically connected to the human body electrode plate;
   a resistance measuring unit for measuring an inter-device electric resistance value as electric resistance between the first electrode and the second electrode and an electrode-to-human body resistance value as electric resistance between the first electrode or the second electrode and the human body electrode;
   a determining unit for determining, when an electric resistance value ratio as a ratio of the inter-device electric resistance value and the electrode-to-human body resistance value decreases, that the first medical device and the second medical device have come into contact with each other; and a warning generating unit for generating a warning when the determining unit determines that the first medical device and the second medical device have come into contact with each other.

2. The medical device system according to claim 1, wherein at least either the first medical device or the second medical device is an active medical device including a driving unit, the medical device system includes a control unit for controlling operation of the driving unit, the control unit is for performing control of the driving unit on the basis of information of a manual-operation input unit, and the manual-operation input unit is for converting physical displacement of an input unit by manual operation into an electric signal.

3. The medical device system according to claim 2, wherein the control unit performs, when the warning is generated by the warning generating unit, control for stopping the operation of the driving unit.

4. The medical device system according to claim 2, wherein the control unit controls, when the warning is generated by the warning generating unit, the driving unit to prohibit at least either the first medical device or the second medical device from moving in a moving direction before reception of the warning.

5. The medical device system according to claim 2, wherein the control unit includes an operation storing unit for storing operation information of the driving unit and controls, when the warning is generated by the warning generating unit, on the basis of the operation information stored by the operation storing unit, the driving unit to return a state of the driving unit to a state before reception of the warning.

6. The medical device system according to claim 5, wherein the control unit performs control for returning a state of the physical displacement of the input device to a state before reception of the warning.

7. The medical device system according to claim 2, wherein the first medical device includes an electric knife, and the control unit controls, on the basis of the warning of the warning generating unit, an electric knife control unit to stop or reduce output of the electric knife.

8. The medical device system according to claim 1, wherein the first medical device or/and the second medical device are projected from a distal end portion of an endoscope and used.

9. The medical device system according to claim 1, wherein the first medical device is an endoscope and the second medical device is projected from a distal end portion of the endoscope and used.

* * * * *